(12) United States Patent
Ichihara et al.

(10) Patent No.: US 10,736,583 B2
(45) Date of Patent: Aug. 11, 2020

(54) MEDICAL IMAGE PROCESSING APPARATUS AND X-RAY CT APPARATUS

(71) Applicants: Canon Medical Systems Corporation, Otawara-shi (JP); FUJITA ACADEMY, Toyoake-shi (JP)

(72) Inventors: Takashi Ichihara, Nagoya (JP); Yoshihiro Ikeda, Sakura (JP); Takuya Sakaguchi, Utsunomiya (JP)

(73) Assignees: Canon Medical Systems Corporation, Otawara-shi (JP); FUJITA ACADEMY, Toyoake-shi (JP)

( * ) Notice: Subject to any disclaimer, the term of this patent is extended or adjusted under 35 U.S.C. 154(b) by 121 days.

(21) Appl. No.: 15/951,334

(22) Filed: Apr. 12, 2018

(65) Prior Publication Data

US 2018/0296169 A1   Oct. 18, 2018

(30) Foreign Application Priority Data

Apr. 12, 2017   (JP) .................................. 2017-079108

(51) Int. Cl.
*A61B 6/03* (2006.01)
*G06T 7/00* (2017.01)
(Continued)

(52) U.S. Cl.
CPC .............. *A61B 6/032* (2013.01); *A61B 6/481* (2013.01); *A61B 6/503* (2013.01); *A61B 6/507* (2013.01); *A61B 6/5217* (2013.01); *A61B 6/541* (2013.01); *G06T 7/0012* (2013.01); *G06T 7/0016* (2013.01); *A61B 6/4078* (2013.01); *A61B 6/4085* (2013.01); *A61B 6/5258* (2013.01); *G06T 11/003* (2013.01);
(Continued)

(58) Field of Classification Search
CPC ......... A61B 6/032; A61B 6/481; A61B 6/503; A61B 6/507; A61B 6/5217; A61B 6/541; A61B 6/4078; A61B 6/4085; A61B 6/5258; G06T 7/0012; G06T 7/0016
See application file for complete search history.

(56) References Cited

U.S. PATENT DOCUMENTS

| | | | |
|---|---|---|---|
| 2006/0173292 A1* | 8/2006 | Baba ...................... | A61B 8/469 600/425 |
| 2012/0065499 A1* | 3/2012 | Chono .................... | A61B 8/00 600/425 |
| 2018/0025493 A1 | 1/2018 | Homma et al. | |

FOREIGN PATENT DOCUMENTS

| | | |
|---|---|---|
| JP | 2012-256175 | 12/2012 |
| WO | WO 2016/157457 A1 | 10/2016 |

\* cited by examiner

*Primary Examiner* — Leon Flores
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry sets a first region of interest in a region corresponding to cardiac muscle on a cross-section of a heart included in image data. The processing circuitry further sets a second region of interest that is larger than the first region of interest in a region including the region. The processing circuitry determines a threshold for determining a range of signal values used for blood flow dynamic analysis on the image data based on a frequency distribution of signal values in the first region of interest. The processing circuitry carries out blood flow dynamic analysis on the second region of interest using signal values included in a range based on the threshold.

20 Claims, 8 Drawing Sheets

(51) Int. Cl.
*A61B 6/00* (2006.01)
*G06T 11/00* (2006.01)
(52) U.S. Cl.
CPC ... *G06T 11/008* (2013.01); *G06T 2207/10081* (2013.01); *G06T 2207/10116* (2013.01); *G06T 2207/30048* (2013.01); *G06T 2207/30104* (2013.01)

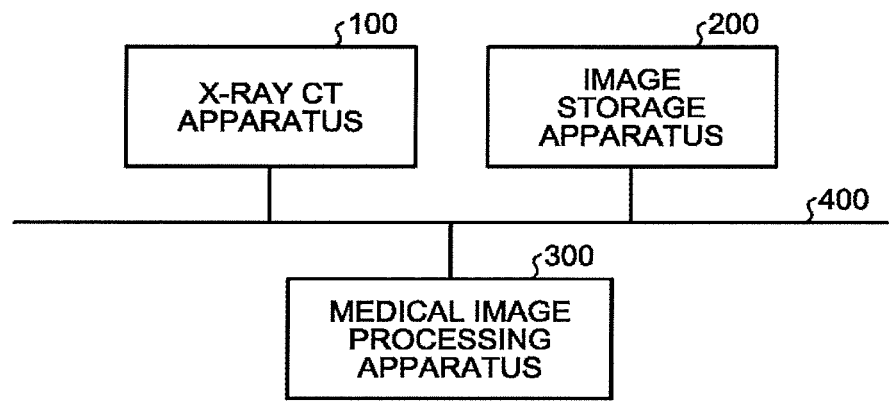
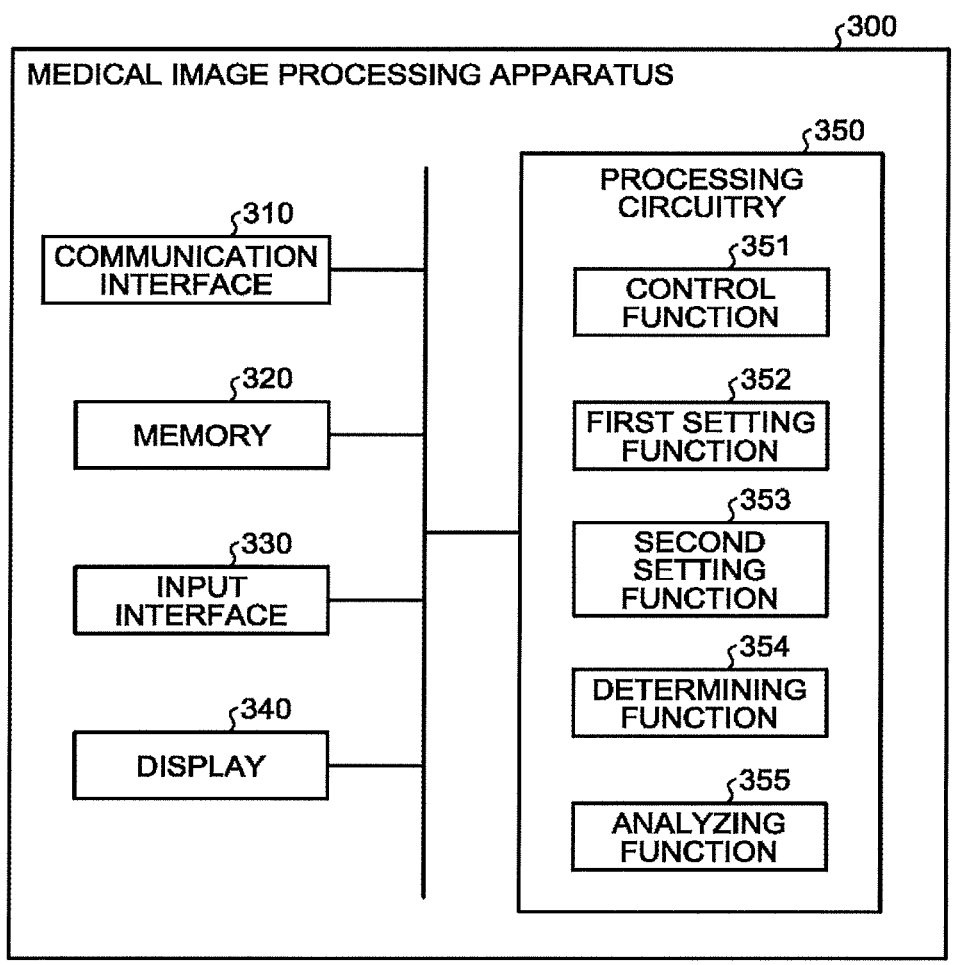

FIG.8
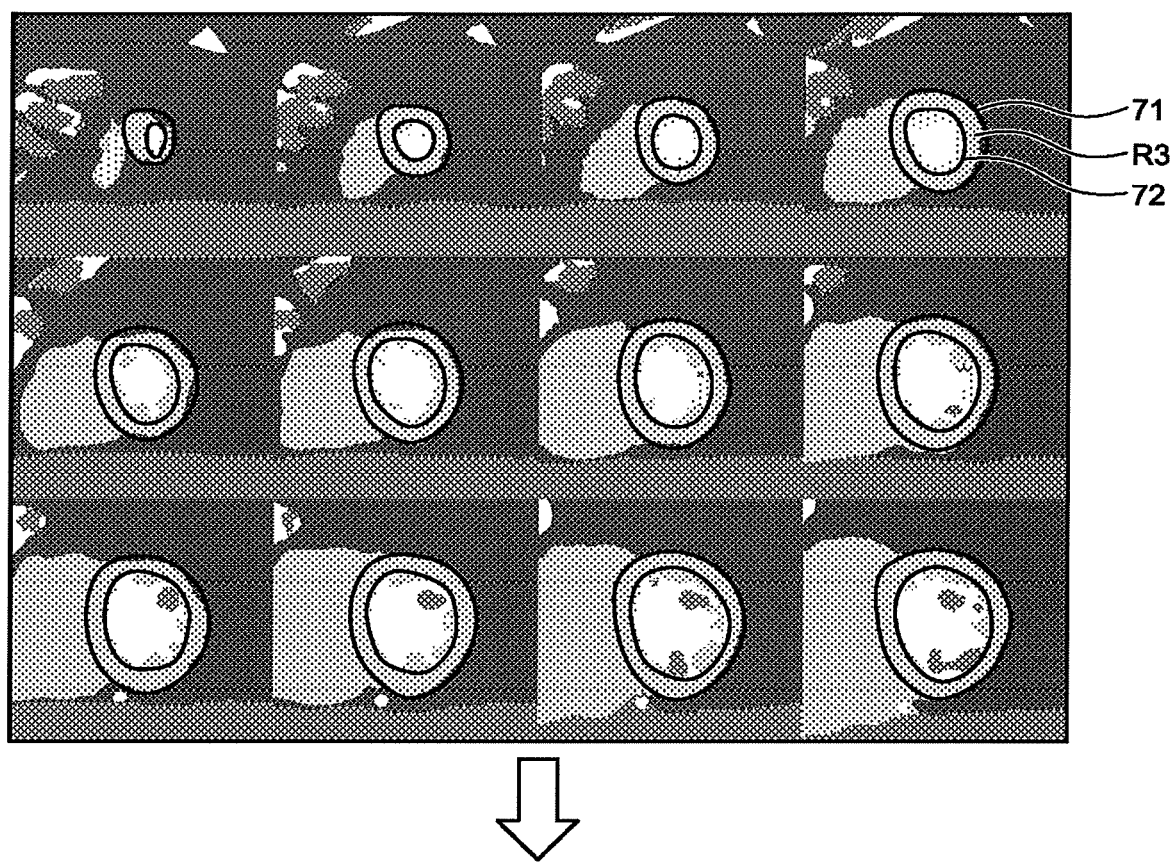
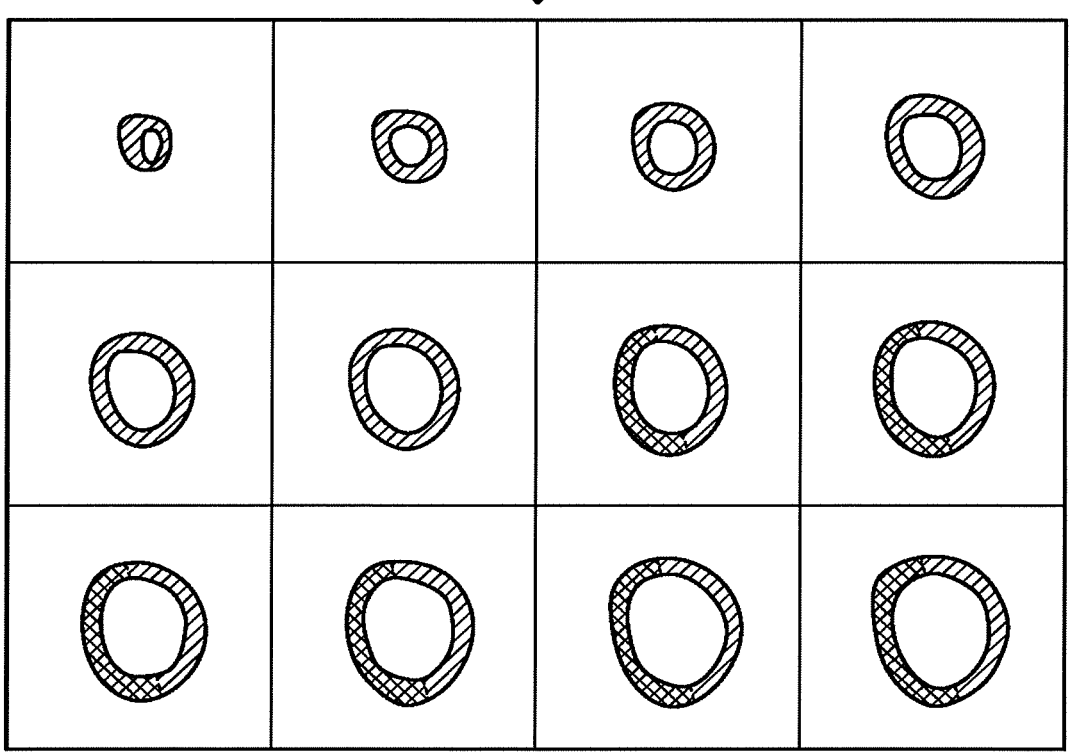

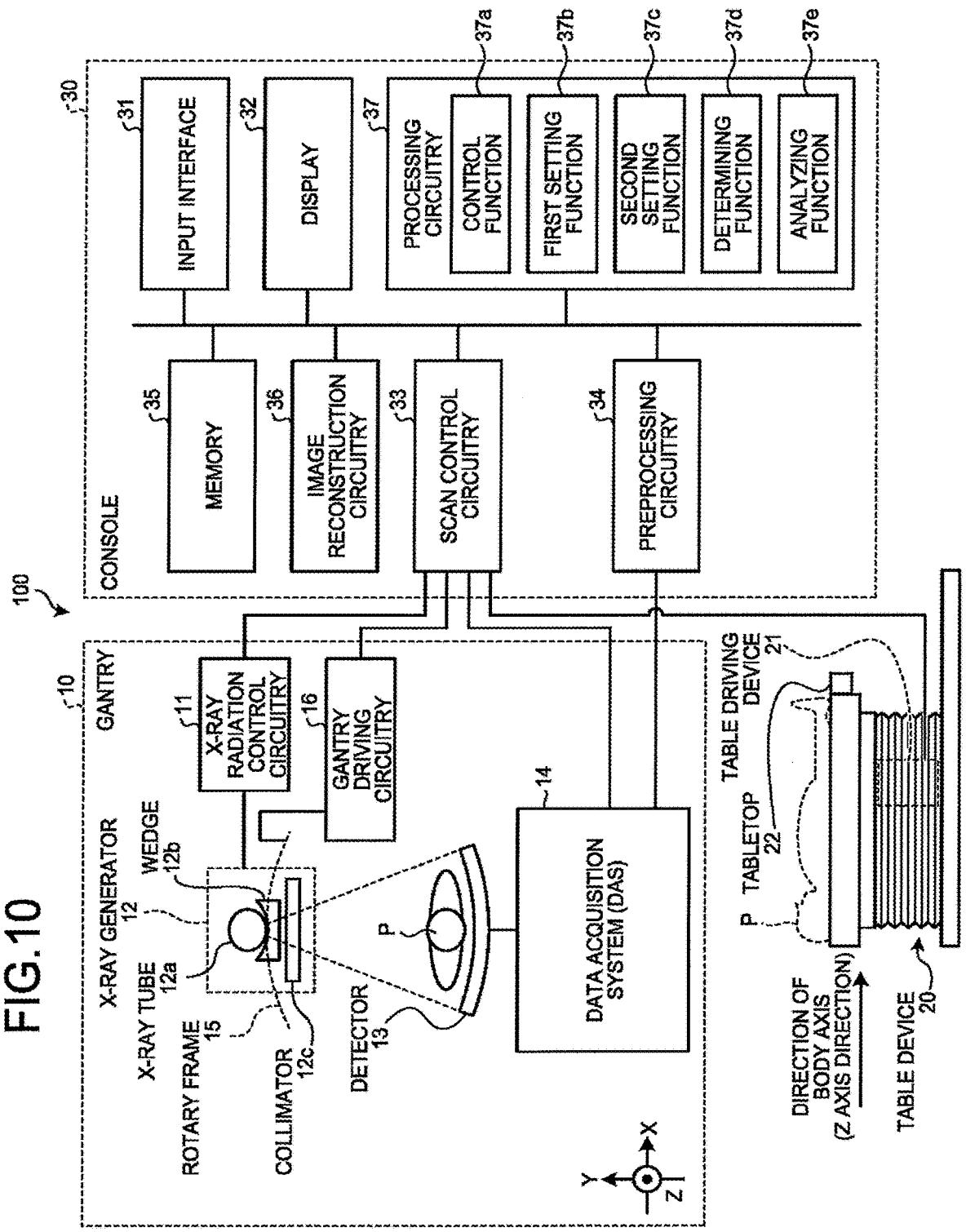

US 10,736,583 B2

MEDICAL IMAGE PROCESSING APPARATUS AND X-RAY CT APPARATUS

CROSS-REFERENCE TO RELATED APPLICATIONS

This application is based upon and claims the benefit of priority from Japanese Patent Application No. 2017-79108, filed on Apr. 12, 2017; the entire contents of which are incorporated herein by reference.

FIELD

Embodiments described herein relate generally to a medical image processing apparatus and an X-ray CT apparatus.

BACKGROUND

An X-ray computed tomography (CT) apparatus is conventionally used for examination of myocardial perfusion. In the examination, for example, a contrast material is injected into a blood vessel, and CT images of a heart collected by the X-ray CT apparatus are analyzed. The amount of blood flow into the cardiac muscle is measured by estimating the amount of the contrast material reaching the cardiac muscle and estimating the amount of blood flow into the cardiac muscle based on the estimated amount of the contrast material.

BRIEF DESCRIPTION OF THE DRAWINGS

FIG. 1 is a drawing of an exemplary configuration of a medical image processing system according to a first embodiment;

FIG. 2 is a drawing of an exemplary configuration of a medical image processing apparatus according to the first embodiment;

FIG. 8 is a drawing of exemplary results of estimation on the amount of blood flow given by an analyzing function according to the first embodiment;

FIG. 10 is a drawing of an exemplary configuration of an X-ray CT apparatus according to a second embodiment.

DETAILED DESCRIPTION

Figure 3:
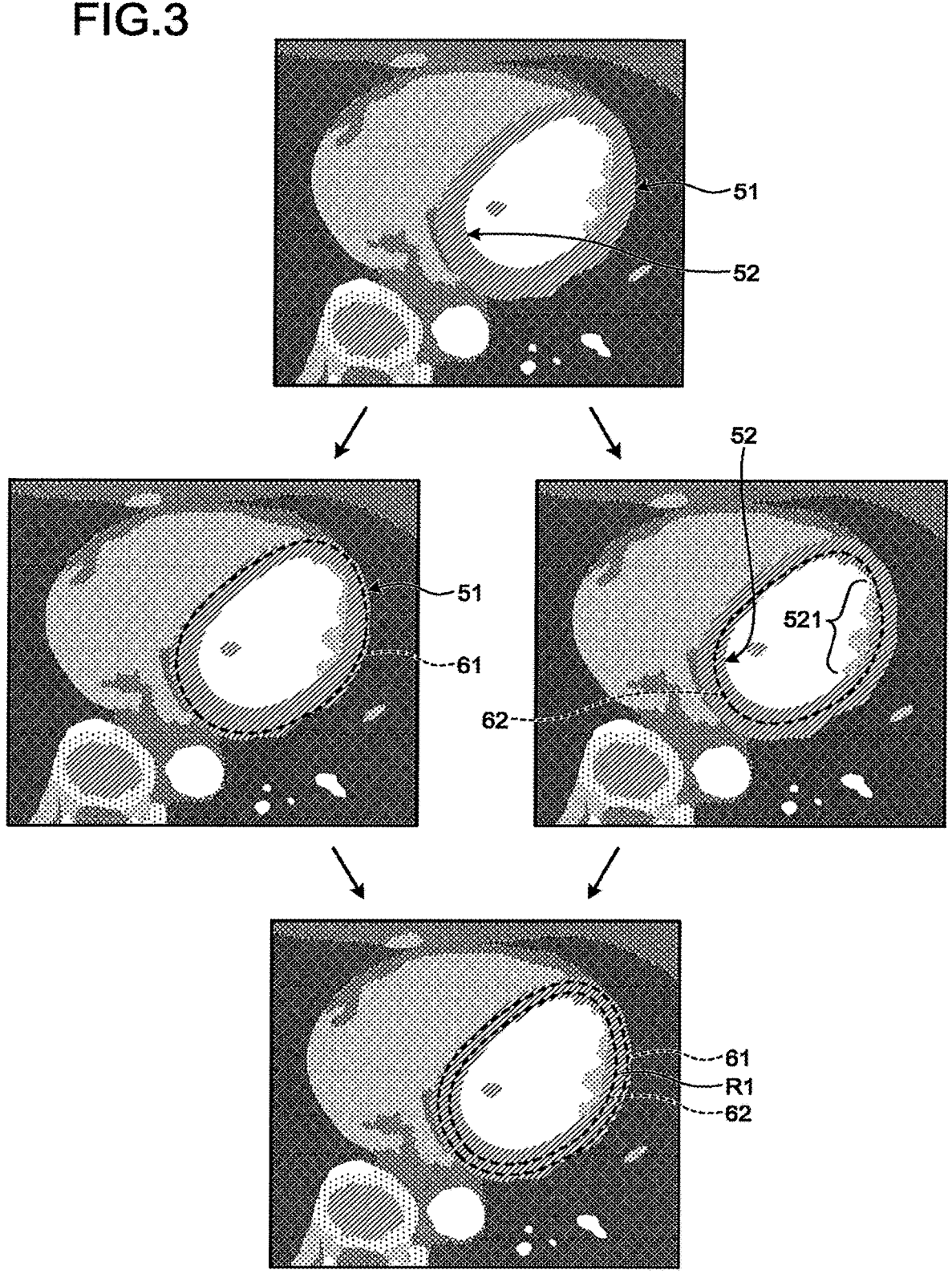
FIG. 3 is an illustrative drawing of exemplary processing performed by a first setting function according to the first embodiment.

According to an embodiment, a medical image processing apparatus includes processing circuitry. The processing circuitry is configured to set a first region of interest in a region corresponding to cardiac muscle on a cross-section of a heart included in image data. The processing circuitry is configured to set a second region of interest that is larger than the first region of interest in a region including the region. The processing circuitry is configured to determine a threshold for determining a range of a signal value used for blood flow dynamic analysis on the image data based on a frequency distribution of a signal value in the first region of interest. The processing circuitry is configured to carry out blood flow dynamic analysis on the second region of interest using signal values included in a range based on the threshold.

Embodiments of a medical image processing apparatus and an X-ray CT apparatus according to the present application will now be described in detail with reference to the accompanying drawings. It should be noted that the medical image processing apparatus and the X-ray CT apparatus according to the present application are not limited by the following embodiments.

First Embodiment

A first embodiment will now be described. In the first embodiment, as an example, a technique disclosed in the present application is applied to a medical image processing apparatus. A medical image processing system including the medical image processing apparatus will now be described as an example.

FIG. 1 is a drawing of an exemplary configuration of a medical image processing system according to the first embodiment. As illustrated in FIG. 1, the image processing system according to the first embodiment includes an X-ray computed tomography (CT) apparatus 100, an image storage apparatus 200, and a medical image processing apparatus 300.

For example, in the medical image processing system, the medical image processing apparatus 300 according to the first embodiment is connected with the X-ray CT apparatus 100 and the image storage apparatus 200 through a network 400 as illustrated in FIG. 1. The image information processing system may be connected with another medical image diagnostic apparatus such as a magnetic resonance imaging (MRI) apparatus, an ultrasound diagnostic apparatus, and a positron emission tomography (PET) apparatus through the network 400.

The X-ray CT apparatus 100 collects CT image data (volume data) of a subject. Specifically, the X-ray CT apparatus 100 rotates an X-ray tube and an X-ray detector with the subject substantially centered, detects X-rays passing through the subject, and collects projection data. The X-ray CT apparatus 100 generates CT image data in time series based on the collected projection data. For example, the X-ray CT apparatus 100 generates CT image data in time series with a region including a heart as a target object.

The X-ray CT apparatus 100 is connected with an injector and an electrocardiograph. The injector injects a contrast material into the subject under control of the X-ray CT apparatus 100. Specifically, the injector is controlled by a control signal received from the X-ray CT apparatus 100 and injects a contrast material into the subject under predetermined conditions. The injector may inject a contrast material into the subject in response to an operation by an operator. The electrocardiograph generates an electrocardiogram by detecting an electrocardiogram (ECG) signal of the subject through electrodes put on the subject and transmits the generated electrocardiogram to the X-ray CT apparatus 100. The X-ray CT apparatus 100 is capable of generating CT image data synchronized with a certain phase on the electrocardiogram wave pattern by controlling X-ray radiation based on the electrocardiogram received from the electrocardiograph. For example, the X-ray CT apparatus 100 collects, at every heartbeat from the subject with the contrast material injected, CT image data of the heart in diastole with the contrast material injected based on synchronization on the electrocardiogram.

The image storage apparatus 200 stores image data collected by various medical image diagnostic apparatus through the network 400. For example, the image storage apparatus 200 is implemented by a computer apparatus such as a server apparatus. In the present embodiment, the image storage apparatus 200 acquires CT image data (volume data) from the X-ray CT apparatus 100 through the network 400 and stores the acquired CT image data in a memory provided inside or outside the apparatus.

The medical image processing apparatus 300 acquires image data from various medical image diagnostic apparatus through the network 400 and performs processing on the acquired image data. For example, the medical image processing apparatus 300 is implemented by a computer apparatus such as a workstation. In the present embodiment, the medical image processing apparatus 300 acquires CT image data from the X-ray CT apparatus 100 or the image storage apparatus 200 through the network 400 and provides various kinds of image processing on the acquired CT image data. The medical image processing apparatus 300 displays, for example, a CT image having undergone image processing and results of analysis obtained from the image processing on a display and others.

FIG. 2 is a drawing of an exemplary configuration of the medical image processing apparatus 300 according to the first embodiment. For example, as illustrated in FIG. 2, the medical image processing apparatus 300 includes a communication interface (I/F) 310, a memory 320, an input interface 330, a display 340, and processing circuitry 350.

The communication interface 310 is connected with the processing circuitry 350. The communication interface 310 controls transmission of various kinds of data to various medical image diagnostic apparatus or the image storage apparatus 200 connected through the network 400 and controls communication with the apparatus. For example, the communication interface 310 is implemented by a network card, a network adaptor, a network interface controller (NIC) and others. In the present embodiment, the communication interface 310 receives CT image data from the X-ray CT apparatus 100 or the image storage apparatus 200 and outputs the received CT image data to the processing circuitry 350.

The memory 320 is connected to the processing circuitry 350 and stores various kinds of data. For example, the memory 320 is implemented by a semiconductor memory element such as a random access memory (RAM) and a flash memory, a hard disk, an optical disk, and the like. In the present embodiment, the memory 320 stores CT image data received from the X-ray CT apparatus 100 and the image storage apparatus 200. For example, the memory 320 stores CT image data sequentially collected by the X-ray CT apparatus 100. For example, the memory 320 stores CT image data of a heart in diastole collected at every heartbeat after injection of a contrast material.

The input interface 330 is connected to the processing circuitry 350. The input interface 330 converts an input operation received from the operator to an electric signal and outputs the signal to the processing circuitry 350. For example, the input interface 330 is implemented by a trackball, a switch button, a mouse, a keyboard, a touchscreen, and the like.

The display 340 is connected to the processing circuitry 350 and displays various kinds of information and images output from the processing circuitry 350. For example, the display 340 is implemented by a liquid crystal display, a cathode ray tube (CRT) monitor, a touchscreen, and the like. For example, the display 340 displays results of analysis obtained based on CT image data and a CT image under display control by the processing circuitry 350.

The processing circuitry 350 controls each component included in the medical image processing apparatus 300 in response to an input operation received from the operator through the input interface 330. For example, the processing circuitry 350 is implemented by a processor. In the present embodiment, the processing circuitry 350 stores CT image data output from the communication interface 310 in the memory 320. The processing circuitry 350 further reads CT image data from the memory 320 and causes the display 340 to display a CT image generated from the read CT image data. The processing circuitry 350 performs various kinds of analytical processing on the CT image data and causes the display 340 to display results of the analysis.

This construction allows the medical image processing apparatus 300 according to the present embodiment to accurately estimate the amount of blood flow. Specifically, in perfusion analysis using a medical image (such as three-dimensional CT image data) including a heart, the medical image processing apparatus 300 accurately estimates the amount of blood flow in cardiac muscle by removing noise included in the image data. The amount of blood flow in the cardiac muscle is estimated based on the concentration (a signal value of the cardiac muscle) of a contrast material in the cardiac muscle. Noise included in the cardiac muscle region on the CT image data causes an error in the results of estimation of the amount of blood flow. The medical image processing apparatus 300 according to the present application therefore removes noise from signal values in the cardiac muscle, thereby accurately estimating the amount of blood flow after the removal.

The medical image processing apparatus 300 according to the present embodiment will now be described in detail. As illustrated in FIG. 2, in the medical image processing apparatus 300 according to the present embodiment, the processing circuitry 350 executes a control function 351, a first setting function 352, a second setting function 353, a determining function 354, and an analyzing function 355. The processing circuitry 350 is an example of processing circuitry in the appended claims.

The control function 351 integrally controls the medical image processing apparatus 300. For example, the control function 351 acquires CT image data from the X-ray CT apparatus 100 or the image storage apparatus 200 through the communication interface 310. For example, the control function 351 acquires CT image data of a heart in diastole collected at every heartbeat after injection of a contrast material. The control function 351 stores the acquired CT image data in the memory 320. The control function 351 generates a CT image from CT image data and controls the display 340 to display the generated CT image. The control function 351 further controls the display 340 to display results of analysis obtained by the analyzing function 355.

On a cross-section of a heart included in the image data, the first setting function 352 sets a first region of interest on an annular region corresponding to the cardiac muscle. Specifically, the first setting function 352 sets the first region of interest by setting boundaries of the cardiac muscle on the cross-section of the heart in a manner excluding signals other than a signal derived from a contrast material flowing into the cardiac muscle. The first setting function 352 sets the first region of interest that includes only the cardiac muscle. As described above, the medical image processing apparatus 300 removes noise from signal values of the cardiac muscle, thereby accurately estimating the amount of blood flow after the removal. The first setting function 352 sets the first region of interest so as to determine a threshold used for processing of removing noise from signal values of the cardiac muscle on the CT image data. In other words, the first setting function 352 sets the first region of interest used for determination of a threshold for judging whether a signal value is appropriate as a value of the cardiac muscle on the CT image.

FIG. 3 is an illustrative drawing of exemplary processing performed by the first setting function 352 according to the first embodiment. In FIG. 3, the first region of interest is set on the cardiac muscle of a left ventricle on a cross-section perpendicular to a cardiac axis. For example, as illustrated in FIG. 3, the first setting function 352 sets the first region of interest on an annular region between a contour 52 representing an inner wall of the cardiac muscle and a contour 51 representing an outer wall of the cardiac muscle of the left ventricle in a manner excluding signals other than a signal derived from a contrast material flowing into the cardiac muscle, on the cross-section of the left ventricle.

For example, as illustrated in the left side drawing in the middle row of FIG. 3, the first setting function 352 sets a boundary 61 inside the contour 51 representing the outer wall of the cardiac muscle. Likewise, as illustrated in the right side drawing in the middle row of FIG. 3, the first setting function 352 sets a boundary 62 outside the contour 52 representing the inner wall of the cardiac muscle. In this manner, as illustrated in the drawing in the bottom row of FIG. 3, the first setting function 352 sets a first region of interest R1 between the boundary 61 and the boundary 62. The boundary 61 and the boundary 62 are set in a manner excluding signals other than a signal derived from a contrast material flowing into the cardiac muscle.

For example, the first setting function 352 sets the outer boundary 61 corresponding to the outer wall of the cardiac muscle in a manner excluding a signal derived from a lumen adjacent to a lumen surrounded by the cardiac muscle from the region surrounded by the boundaries of the cardiac muscle. More specifically, when setting a first region of interest R1 on the cardiac muscle in the left ventricle, the first setting function 352 sets the boundary 61 in a manner not including a signal derived from the lumen of the right ventricle in the first region of interest R1. A contrast material included in the lumen of the right ventricle may cause an artifact resulting from the contrast material in the region of the cardiac muscle of the left ventricle. The first setting function 352 therefore sets the boundary 61 in a manner excluding a signal in the lumen of the right ventricle and a signal on the cardiac muscle region derived from the signal of the lumen of the right ventricle, from the first region of interest.

Furthermore, for example, the first setting function 352 sets the inner boundary 62 corresponding to the inner wall of the cardiac muscle in a manner excluding a signal derived from a lumen surrounded by the cardiac muscle from the region surrounded by the boundaries of the cardiac muscle. More specifically, when setting the first region of interest on the cardiac muscle in the left ventricle, the first setting function 352 sets the boundary 62 in a manner not including a signal derived from the lumen of the left ventricle in the first region of interest R1. As indicated by a region 521 illustrated in the right side drawing in the middle row of FIG. 3, the contour 52 representing the inner wall of the left ventricle may have pleats (projections and recesses) because of an artifact resulting from a contrast material in the right ventricle and a signal derived from the shape of the intima of the left ventricle. The first setting function 352 therefore sets the inner boundary 62 of the cardiac muscle in a manner not including signals of these pleats.

As described above, the first setting function 352 sets an annular region formed by setting the boundary 61 and the boundary 62 in a manner excluding signals other than a signal derived from a contrast material flowing into the cardiac muscle, as the first region of interest R1. The first setting function 352 can set the first region of interest by various methods. An exemplary method of setting the first region of interest will now be described.

For example, the first setting function 352 sets the first region of interest by extracting the cardiac muscle on a cross-section of a heart, performing dilation processing on an inner contour corresponding to the inner wall of the extracted cardiac muscle, and performing reduction processing on an outer contour corresponding to the outer wall of the cardiac muscle. The first setting function 352 extracts the contours 51 and 52 of the cardiac muscle using a known algorithm for extracting cardiac muscle. The first setting function 352 performs morphology processing on each of the extracted contours 51 and 52 and sets the boundary 61 and the boundary 62. For example, the first setting function 352 reduces a region surrounded by the contour 51 by performing erosion processing on the region and sets the outer contour of the reduced region as the boundary 61. The first setting function 352 further dilates a region surrounded by the contour 52 by performing dilation processing on the region and sets the outer contour of the dilated region as the boundary 62. Any number of surrounding pixels serving as target objects of the morphology processing can be set. For example, two or three pixels are set.

The first setting function 352 further extracts the cardiac muscle on the cross-section of a heart, deforms a region surrounded by contours of the extracted cardiac muscle such that a frequency distribution of signal values in the region surrounded by the contours is approximate to the normal distribution, and sets the deformed region as a first region of interest. The first setting function 352 extracts the contours 51 and 52 of the cardiac muscle by using a known algorithm for extracting cardiac muscle. The first setting function 352 generates a histogram for an annular region surrounded by the extracted contours 51 and 52, reduces the annular region such that the generated histogram is approximate to the normal distribution, and sets the first region of interest. For example, the first setting function 352 reduces the contour 51 and dilates the contour 52 to make the histogram approximate to the normal distribution. The first setting function 352 sets an annular region with the histogram approximate to the normal distribution as the first region of interest R1.

The first setting function 352 can set the first region of interest in response to an operation by an operator. In this case, for example, the input interface 330 receives an input operation from the operator. The first setting function 352 performs processing in response to the operation received by the input interface 330. For example, the display 340 displays a cross-sectional image of cardiac muscle as illustrated in FIG. 3. The operator refers to the cross-sectional image displayed on the display 340 and makes a designation operation for designating the boundary 61 and the boundary 62 through the input interface 330. The first setting function 352 sets the annular region surrounded by the boundary 61 and the boundary 62 received by the input interface 330 as the first region of interest R1.

For example, the input interface 330 receives an operation for executing the above-described morphology processing. The first setting function 352 performs the morphology processing in response to an operation received by the input interface 330. For example, the display 340 displays ellipses representing the contour 51 and the contour 52 on a cross-sectional image of cardiac muscle as illustrated in FIG. 3. The operator refers to the ellipses representing the contour 51 and the contour 52 on the cross-sectional image displayed on the display 340 and makes an input operation for executing the erosion processing and an input operation for executing the dilation processing through the input interface 330. The first setting function 352 performs the morphology processing in response to the input operation received by the input interface 330 and sets the first region of interest R1.

The known algorithm for extracting cardiac muscle may be modified so as to directly set the above-described first region of interest. For example, the known algorithm for extracting cardiac muscle is modified such that the contour 51 corresponding to the outer wall of the cardiac muscle is extracted with a signal derived from an adjacent lumen excluded from the region of the cardiac muscle and that the contour 52 corresponding to the inner wall of the cardiac muscle is extracted with a signal derived from the lumen excluded from the region of the cardiac muscle. The first setting function 352 extracts the cardiac muscle based on the modified algorithm for extracting cardiac muscle, thereby setting the first region of interest R1 without having the above-described processing.

Figure 4:
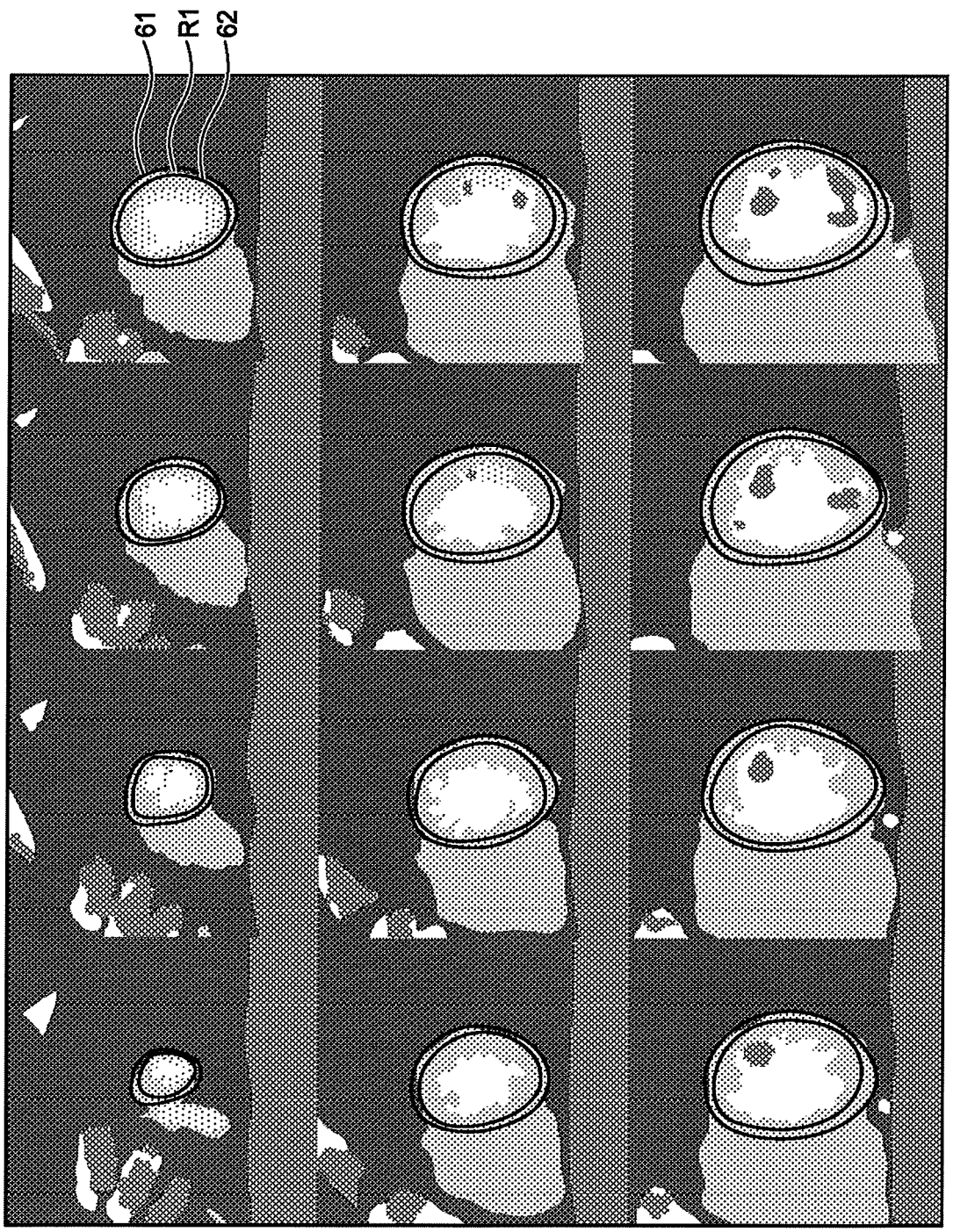
FIG. 4 is a drawing of an exemplary first region of interest on each cross-section of a cardiac muscle according to the first embodiment.

The first setting function 352 sets the first region of interest R1 on each cross-section of the cardiac muscle. FIG. 4 is a drawing of an exemplary first region of interest on each cross-section of the cardiac muscle according to the first embodiment. In FIG. 4, the first region of interest is set on each of 12 cross-sections perpendicular to the cardiac axis on a single CT image data piece out of a plurality of CT image data pieces collected in diastole periods. For example, as illustrated in FIG. 4, the first setting function 352 sets the first region of interest R1 on each of 12 cross-sections of the left ventricle using the above-described various setting methods.

Likewise, the first setting function 352 sets the first regions of interest R1 on each of the CT image data pieces collected in individual diastole periods. In other words, as illustrated in FIG. 4, the first setting function 352 sets the first regions of interest on individual cross-sections on each CT image data piece collected in a corresponding timing. The first setting function 352 can set the first regions of interest on each of CT image data pieces. In another manner, the first setting function 352 can set the first region of interest R1 by aligning images between CT image data pieces and using the results.

As described above, each CT image data piece on which the first regions of interest R1 are set includes a cardiac image photographed in a certain cardiac period (for example, in diastole) by using electrocardiogram gating. A difference in the shape of the heart between CT image data pieces is considered to be small. The first setting function 352 thus modifies a first region of interest R1 set for a certain CT image data piece based on the result of alignment between CT image data pieces and sets the first region of interest R1 for other CT image data pieces. For example, the first setting function 352 sets the first region of interest R1 on each cross-section on a single CT image data piece (a first CT image data piece). The first setting function 352 modifies the set first region of interest R1 based on the result of alignment between the first CT image data piece and another CT image data piece (a second CT image data piece) and sets the first region of interest R1 on the second CT image data piece. In other words, the first setting function 352 modifies the first region of interest R1 on each cross-section on the first CT image data piece based on the result of alignment and sets the modified first region of interest R1 for corresponding cross-section on the second CT image data piece. The result of alignment between CT image data pieces may be acquired with the first setting function 352 carrying out the alignment. In another manner, a result of alignment carried out in blood flow dynamic analysis may be reused.

The first setting function 352 can apply the first region of interest R1 set for the first CT image data piece to other CT image data pieces by assuming that there are no differences between CT image data pieces.

The first setting function 352 can set the first region of interest in response to an operation by an operator. For example, the display 340 displays cross-sectional images of cardiac muscle as illustrated in FIG. 3 on each CT image data piece. The operator refers to cross-sectional images displayed on the display 340 and makes a designation operation for designating the boundary 61 and the boundary 62 on each cross-section of the CT image data piece through the input interface 330. The first setting function 352 sets an annular region surrounded by the boundary 61 and the boundary 62 received by the input interface 330 as the first region of interest R1.

The operator may modify the first region of interest R1 through the input interface 330. For example, the first setting function 352 sets the first regions of interest R1 on a plurality of CT image data pieces. The operator refers to the first region of interest R1 on each CT image data piece set by the first setting function 352. When determining that the set region is not appropriate, the operator can modify the first region of interest R1 through the input interface 330.

In the above-described example, the first region of interest R1 is set on CT image data in a certain cardiac phase (such as in diastole). The first setting function 352 can further set the first region of interest R1 on CT image data in a different cardiac phase. For example, the first setting function 352 sets the first region of interest R1 on CT image data in a certain cardiac phase. The first setting function 352 identifies a deformation pattern of the cardiac muscle by a pattern matching method and deforms the set first region of interest R1 based on the identified deformation pattern, thereby setting the first region of interest R1 on CT image data in a different cardiac phase. When setting the first region of interest R1 on CT image data in a different cardiac phase, the operator can modify the first region of interest R1 through the input interface 330.

Referring back to FIG. 2, the second setting function 353 sets a second region of interest that is larger than the first region of interest in a region including the annular region. Specifically, the second setting function 353 sets an annular region including the whole of cardiac muscle as the second region of interest. In other words, the second setting function 353 sets a region to be a target object on which a later-described blood flow value is estimated. For example, the second setting function 353 sets the second region of interest using a known algorithm for extracting cardiac muscle. The second region of interest may be set either before or after setting of the first region of interest or after the later-described blood flow dynamic analysis. An exemplary second region of interest will be described later.

The determining function 354 determines a threshold for determining a range of signal values used for the blood flow dynamic analysis carried on image data based on the frequency distribution of signal values in the first region of interest. Specifically, the determining function 354 determines a threshold for judging whether a signal value is appropriate as a value of the cardiac muscle on CT image data. In other words, the determining function 354 determines a threshold for setting a target range of CT values used for estimation of a blood flow value. For example, the determining function 354 generates a histogram of CT values in each first region of interest set by the first setting function 352 and sets a threshold based on the generated histogram.

Figure 5:
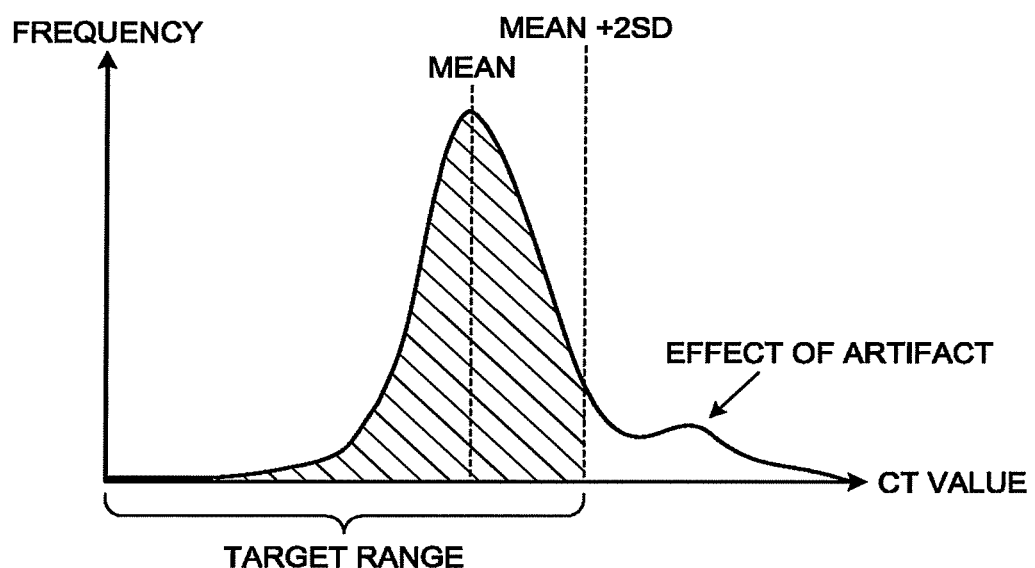
FIG. 5 is an illustrative drawing of exemplary determination of a threshold by a determining function according to the first embodiment.

FIG. 5 is an illustrative drawing of exemplary determination of a threshold by the determining function 354 according to the first embodiment. For example, the determining function 354 generates a histogram as illustrated in FIG. 5 on each first region of interest R1 and determines a threshold for the first region of interest R1 based on the generated histogram. For example, the determining function 354 temporarily assumes a histogram of CT values in the first region of interest R1 to be a normal distribution. As illustrated in FIG. 5, the determining function 354 sets "a mean value+2SD" as a threshold. Because the first region of interest R1 is set in a manner excluding signals other than a signal derived from a contrast material flowing into the cardiac muscle, the histogram of CT values in the first region of interest R1 indicates a distribution of signals exclusively derived from the contrast material in the cardiac muscle. In this manner, setting a threshold based on the histogram allows the threshold to remove only noise and keep signals derived from the contrast material in the cardiac muscle. As an example in the present embodiment, a threshold is determined using a mean value; however, a method of setting a threshold is not limited thereto. For example, a representative value on a histogram determined using the standard deviation or the variance instead of using a mean value may be set as a threshold.

As illustrated in FIG. 5, because a signal of a contrast material in the lumen of cardiac muscle and an artifact derived from the contrast material in the lumen are represented as high CT values, these signals can be effectively removed by setting a threshold based on a histogram of CT values in the first region of interest R1. The determining function 354 determines only a value higher than the mean value to be a threshold on the histogram of signal values in the first region of interest R1. In other words, the determining function 354 sets a threshold only at a side with values higher than the mean value and does not set a threshold at a side with values lower than the mean value so as not to exclude a region (a region with lower CT values) where myocardial ischemia occurs.

The determining function 354 generates a histogram as illustrated in FIG. 5 for the first region of interest R1 set on each of cross-sections on a plurality of CT image data pieces and determines a threshold based on the generated histogram. The determining function 354 sets a target range of CT values used for estimation of a blood flow value on each of the cross-sections on the CT image data pieces.

Figure 6:
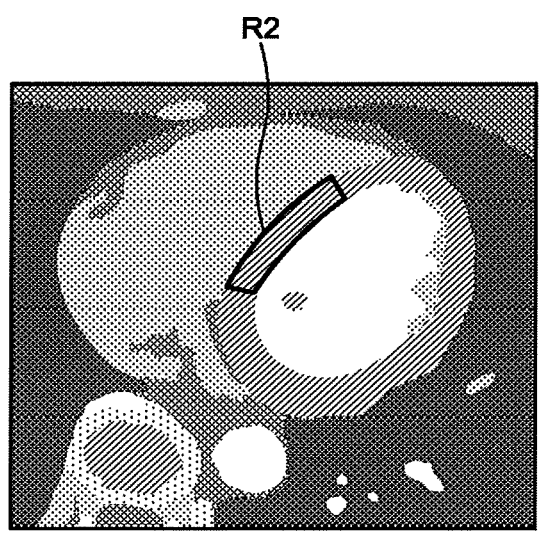
FIG. 6 is a drawing of another example of the first region of interest set by the first setting function according to the first embodiment.

In the above described examples, one first region of interest is set for one annular region. The embodiment is, however, not limited thereto, and for example, a plurality of first regions of interest may be set for an annular region. For example, the first setting function 352 divides an annular region into a plurality of partial regions and sets a first region of interest for each partial region. FIG. 6 is a drawing of another example of the first region of interest set by the first setting function 352 according to the first embodiment. For example, as illustrated in FIG. 6, the first setting function 352 sets a first region of interest R2 including a part of an annular region corresponding to cardiac muscle. Likewise, the first setting function 352 sets a plurality of first regions of interest R2 including individual parts of the annular region corresponding to the cardiac muscle along the annular region.

When the first setting function 352 sets a plurality of first regions of interest for an annular region, the second setting function 353 sets second regions of interest for the individual first regions of interest. The determining function 354 determines a threshold for each of the first regions of interest.

Referring back to FIG. 2, the analyzing function 355 carries out the blood flow dynamic analysis using a signal value included in a range determined based on the threshold. Specifically, the analyzing function 355 removes noise on each cross-section of CT image data using the threshold and carries out the blood flow dynamic analysis using the CT image data with noise removed. The analyzing function 355 excludes CT values exceeding a determined threshold, "a mean value+2SD", on each cross-section of original CT image data and carries out the blood flow dynamic analysis using the cross-section with the CT values excluded. Pixels with CT values excluded may be handled as deficient pixels, or the CT values may be interpolated by CT values of surrounding pixels. When interpolated by CT values of surrounding pixels, for example, the CT value may be interpolated by a mean value of the surrounding pixels.

For example, the analyzing function 355 aligns a plurality of CT image data pieces collected in diastole periods and associates cross-sections with one another between the CT image data pieces. The analyzing function 355 generates a time density curve (TDC) of a contrast material for each pixel associated between the CT image data pieces on a cross-section with noise removed. The analyzing function 355 generates a TDC indicating density variation (time variation of a CT value derived from a contrast material) of the contrast material in a region exclusively including cardiac muscle.

The analyzing function 355 further generates a time density curve of a contrast material in the lumen of the left ventricle on each of CT image data pieces with cross-sections associated with one another. The analyzing function 355 further calculates a conversion table for converting a CT value on the cardiac muscle into the amount of blood flow based on the TDC of the lumen of the left ventricle, a move constant, which is a constant for the contrast material moving from capillary to cardiomyocytes, and others. The analyzing function 355 is capable of estimating the amount of blood flow based on the TDC of the cardiac muscle and the conversion table.

Figure 7:
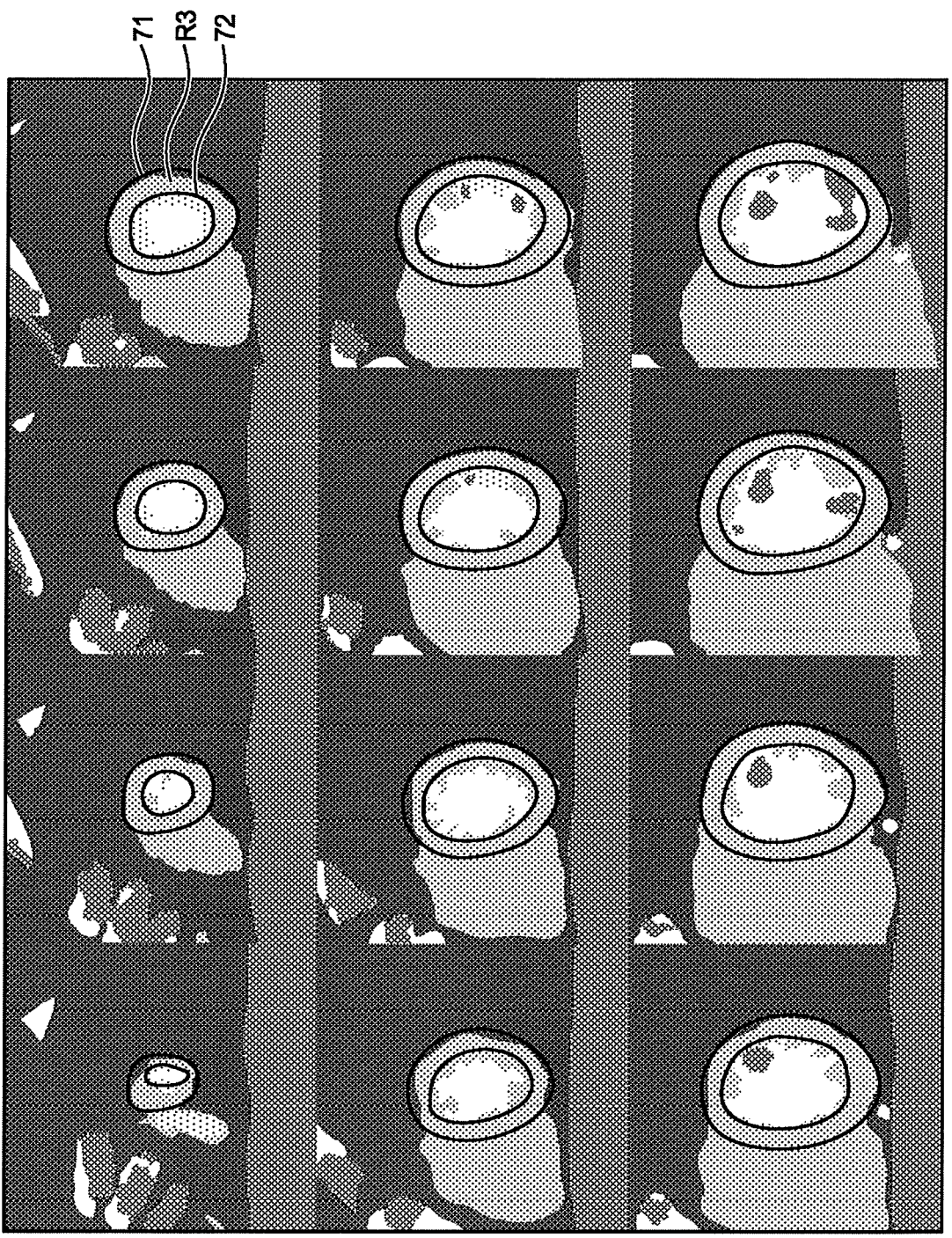
FIG. 7 is a drawing of an exemplary second region of interest set by a second setting function according to the first embodiment.

The analyzing function 355 estimates the amount of blood flow on a second region of interest set by the second setting function 353. FIG. 7 is a drawing of an exemplary second region of interest set by the second setting function 353 according to the first embodiment. In FIG. 7, the second region of interest is set on each of 12 cross-sections perpendicular to the cardiac axis on a single CT image data piece out of a plurality of CT image data pieces collected in individual diastole periods. For example, the second setting function 353 sets a second region of interest R3 on each of 12 cross-sections of the left ventricle as illustrated in FIG. 7.

The second setting function 353 extracts, for example, a boundary 71 corresponding to the outer wall and a boundary 72 corresponding to the inner wall of the cardiac muscle using a known algorithm for extracting cardiac muscle. The second setting function 353 sets a region between the boundary 71 and the boundary 72 as the second region of interest R3. When a plurality of first regions of interest are set for an annular region corresponding to the cardiac muscle, the second setting function 353 sets a plurality of second regions of interest in a manner including the individual first regions of interest. In this case, the first regions of interest and the second regions of interest are set, for example, for each segment defined by the American Heart Association (AHA).

The analyzing function 355 estimates the amount of blood flow in the second region of interest set by the second setting function 353. Specifically, the analyzing function 355 estimates the amount of blood flow by carrying out the blood flow dynamic analysis on the second region of interest using a signal value included in a range determined based on a threshold. More specifically, the analyzing function 355 estimates the amount of blood flow in the cardiac muscle by converting a CT value based on the TDC for the region exclusively including the cardiac muscle with noise removed into the amount of blood flow using a conversion table for converting a CT value of the cardiac muscle into the amount of blood flow. In other words, the analyzing function 355 can accurately estimate the amount of blood flow by using a CT value based on the TDC with noise removed.

The analyzing function 355 is capable of providing the results of estimation of the amount of blood flow in various forms. FIG. 8 is a drawing of exemplary results of estimation of the amount of blood flow given by the analyzing function 355 according to the first embodiment. In FIG. 8, the amount of blood flow is estimated on the second region of interest R3 set in FIG. 7. For example, the analyzing function 355 extracts a CT value at the time point indicated in FIG. 8 from the TDC on each pixel included in the second region of interest R3 and acquires the amount of blood flow corresponding to the extracted CT value from the conversion table. The analyzing function 355 generates a blood-flow value image where each pixel included in the second region of interest R3 is displayed in color as illustrated in the lower drawing of FIG. 8 using a color bar associating a value indicative of the amount of blood flow with a color. The control function 351 controls the display 340 to display the blood-flow value image generated by the analyzing function 355. The control function 351 is capable of causing the display 340 to display both the first region of interest and the second region of interest. For example, the control function 351 causes the display 340 to display a display image having the first region of interest and the second region of interest displayed on a cross-section image of a heart.

The analyzing function 355 is capable of generating blood-flow value images as illustrated in FIG. 8 by carrying out the above-described blood flow dynamic analysis on each CT image data piece collected in a plurality of time points. The analyzing function 355 is capable of generating a blood-flow value image presented using the above-described color bar and also capable of generating a blood-flow value image where a difference in the value indicative of the amount of blood flow is presented using a gray scale. The analyzing function 355 is further capable of generating a blood-flow value image where a value of the amount of blood flow indicated in ml/100 g/min is superimposed on the second region of interest R3.

Figure 9:
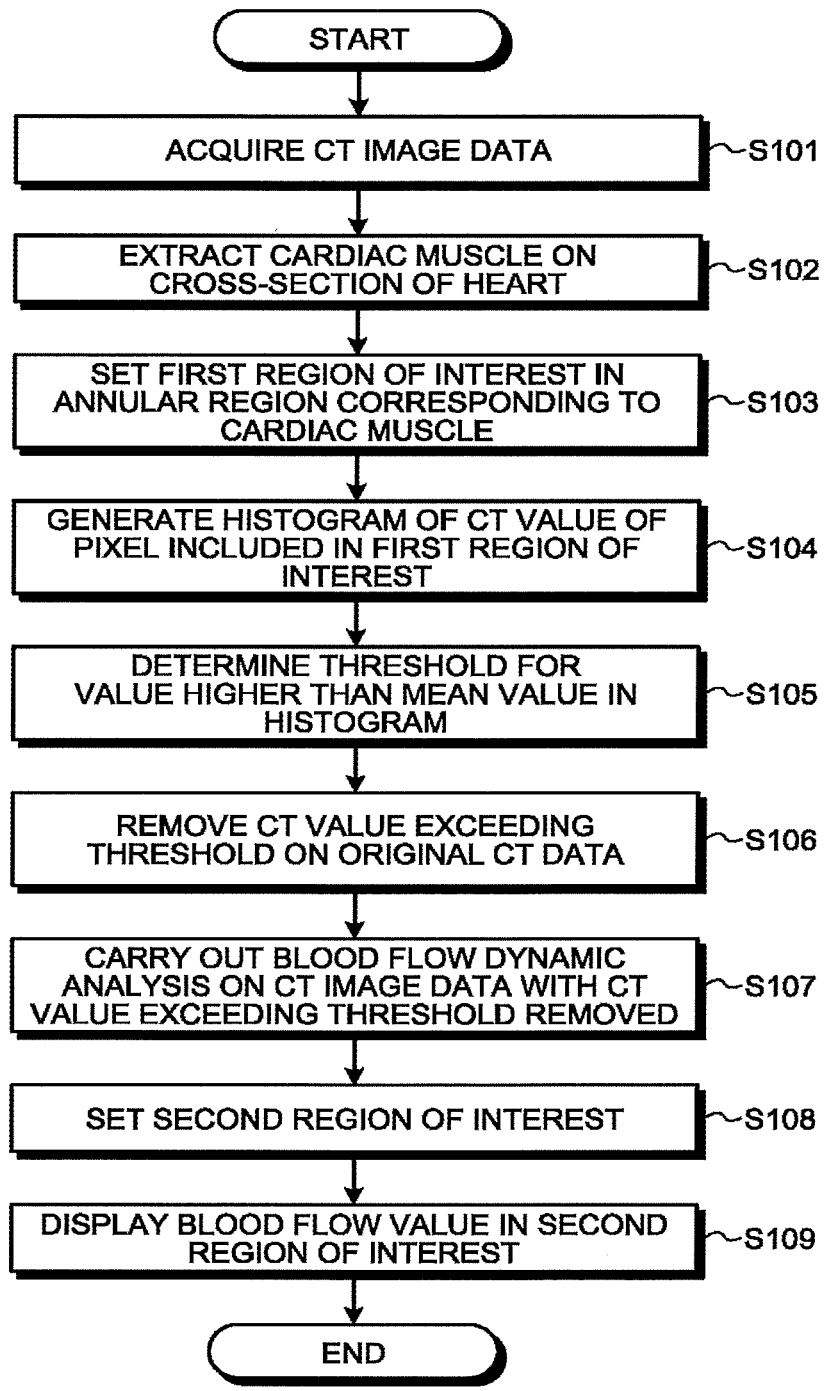
FIG. 9 is a flowchart of a processing procedure carried out by the medical image processing apparatus according to the first embodiment.

A processing procedure carried out by the medical image processing apparatus 300 according to the first embodiment will now be described. FIG. 9 is a flowchart of a processing procedure carried out by the medical image processing apparatus 300 according to the first embodiment. Step S101 and Step S109 illustrated in FIG. 9 are implemented, for example, with the processing circuitry 350 reading out a computer program corresponding to the control function 351 from the memory 320. Step S102 and Step S103 are implemented, for example, with the processing circuitry 350 reading out a computer program corresponding to the first setting function 352 from the memory 320. Step S104 and Step S105 are implemented, for example, with the processing circuitry 350 reading out a computer program corresponding to the determining function 354 from the memory 320. Step S106 and Step S107 are implemented, for example, with the processing circuitry 350 reading out a computer program corresponding to the analyzing function 355 from the memory 320. Step S108 are implemented, for example, with the processing circuitry 350 reading out a computer program corresponding to the second setting function 353 from the memory 320.

In the medical image processing apparatus 300 according to the present embodiment, the processing circuitry 350 acquires CT image data from the X-ray CT apparatus 100 or the image storage apparatus 200 (Step S101). The processing circuitry 350 extracts cardiac muscle on a cross-section of a heart included in the acquired CT image data (Step S102) and sets a first region of interest in an annular region corresponding to the cardiac muscle (Step S103). The processing circuitry 350 generates a histogram of CT values of pixels included in the set first region of interest (Step S104) and determines a threshold applied to values higher than a mean value in the generated histogram (Step S105).

The processing circuitry 350 removes CT values exceeding the threshold on the original CT image data (Step S106) and carries out the blood flow dynamic analysis (generates a time density curve for a contrast material) on the CT image data with CT values exceeding the threshold removed (Step S107). The processing circuitry 350 sets a second region of interest (Step S108) and causes the display 340 to display a value indicative of the amount of blood flow in the set second region of interest (Step S109).

As described above, according to the first embodiment, the first setting function 352 sets a first region of interest in an annular region corresponding to the cardiac muscle on a cross-section of the heart included in the CT image data. The second setting function 353 sets a second region of interest that is larger than the first region of interest in a region including the annular region. The determining function 354 determines a threshold for determining a range of signal values used for the blood flow dynamic analysis performed on CT image data based on the histogram of signal values in the first region of interest. The analyzing function 355 carries out the blood flow dynamic analysis on the second region of interest using a signal value included in the range determined based on the threshold. The medical image processing apparatus 300 according to the first embodiment is capable of carrying out the blood flow dynamic analysis based on a signal value in the region exclusively including the cardiac muscle, which is, based on a signal value with noise removed and is accordingly capable of accurately estimating the amount of blood flow.

According to the first embodiment, the first setting function 352 sets a first region of interest by setting boundaries of cardiac muscle on a cross-section in a manner excluding signals other than a signal derived from a contrast material flowing into the cardiac muscle. In this manner, the medical image processing apparatus 300 according to the first embodiment is capable of efficiently removing noise included in image data.

According to the first embodiment, the first setting function 352 sets the first region of interest by extracting cardiac muscle on a cross-section of the heart, providing dilation processing on the inner contour corresponding to the inner wall of the extracted cardiac muscle, and providing reduction processing on the outer contour corresponding to the outer wall of the cardiac muscle. This construction allows the medical image processing apparatus 300 according to the first embodiment to easily set a first region of interest.

According to the first embodiment, the input interface 330 receives an input operation from an operator. The first setting function 352 provides dilation processing and reduction processing in response to an input operation received by the input interface 330. This construction allows the medical image processing apparatus 300 according to the first embodiment to easily adjust morphology processing.

According to the first embodiment, the first setting function 352 extracts cardiac muscle on a cross-section of a heart, deforms a region surrounded by contours of the extracted cardiac muscle such that a histogram of signal values in the region surrounded by the contours is approximate to the normal distribution, and sets the deformed region as a first region of interest. This construction allows the medical image processing apparatus 300 according to the first embodiment to accurately set the first region of interest based on a signal value.

According to the first embodiment, the first setting function 352 sets an inner boundary corresponding to the inner wall of the cardiac muscle in a manner excluding signals derived from a lumen surrounded by the cardiac muscle from a region surrounded by boundaries of the cardiac muscle. The first setting function 352 further sets an outer boundary corresponding to the outer wall of the cardiac muscle in a manner excluding signals derived from a lumen adjacent to the lumen surrounded by the cardiac muscle from the region surrounded by boundaries of the cardiac muscle. This construction allows the medical image processing apparatus 300 according to the first embodiment to set a first region of interest with signals likely to be included as noise removed.

Furthermore, according to the first embodiment, the first setting function 352 divides an annular region into a plurality of partial regions and sets the first region of interest for each of the partial regions. The second setting function 353 sets a second region of interest for each of the partial regions. The medical image processing apparatus 300 according to the first embodiment is therefore capable of setting the first region of interest for each preset segment and carrying out analysis focused on a difference in a staining pattern of a contrast material.

According to the first embodiment, the determining function 354 determines a threshold on a histogram of signal values in the first region of interest using a mean value, the standard deviation, or the variance. The analyzing function 355 carries out the blood flow dynamic analysis on a second region of interest using a signal value lower than the threshold. This construction therefore allows the medical image processing apparatus 300 according to the first embodiment to provide information on the amount of blood flow with only signals corresponding to noise removed without excluding a region suspected of ischemia.

Second Embodiment

The first embodiment has been described as above; however, the present application is implemented in various different forms other than the first embodiment.

In the first embodiment, cardiac muscle in the left ventricle is a target object. The embodiment is, however, not limited thereto, and for example, the cardiac muscle in the right ventricle may be a target object.

In the first embodiment, each of the outer boundary and the inner boundary of the cardiac muscle is set in a manner removing noise. The embodiment is, however, not limited thereto, and for example, either one of the boundaries may be set in a manner removing noise.

In the first embodiment, the medical image processing apparatus 300 performs various kinds of processing. The embodiment is, however, not limited thereto, and for example, the X-ray CT apparatus 100 may perform various kinds of processing. FIG. 10 is a drawing of an exemplary configuration of the X-ray CT apparatus 100 according to the second embodiment.

As illustrated in FIG. 10, the X-ray CT apparatus 100 according to the second embodiment includes a gantry 10, a table device 20, and a console 30. Although not illustrated, the X-ray CT apparatus 100 further includes an injector and an electrocardiograph. The gantry 10 is an apparatus that irradiates a subject (patient) P with X-rays, detects X-rays passing through the subject P, and outputs the detected X-rays to the console 30. The gantry 10 includes X-ray radiation control circuitry 11, an X-ray generator 12, a detector 13, a data acquisition system (DAS) 14, a rotary frame 15, and gantry driving circuitry 16.

The rotary frame 15 is an annular circular frame that supports the X-ray generator 12 and the detector 13 in a manner facing each other with the subject P interposed therebetween and is rotated at high speed on a circular orbit with the subject P centered by the later-described gantry driving circuitry 16.

The X-ray radiation control circuitry 11 is circuitry that controls a high-voltage generator (not illustrated) and supplies high voltage to an X-ray tube 12a. The X-ray tube 12a generates X-rays using high voltage supplied from the X-ray radiation control circuitry 11. The X-ray radiation control circuitry 11 adjusts the amount of X-ray radiation on the subject P by adjusting tube voltage and tube current supplied to the X-ray tube 12a under control of later-described scan control circuitry 33.

The X-ray radiation control circuitry 11 further switches a wedge 12b. The X-ray radiation control circuitry 11 adjusts the radiation range (the fan angle and the cone angle) of X-rays by adjusting the size of aperture of a collimator 12c. In the present embodiment, an operator may manually switch a plurality of types of wedge.

The X-ray generator 12 is a device that generates X-rays and irradiates the subject P with the generated X-rays. The X-ray generator 12 includes the X-ray tube 12a, the wedge 12b, and the collimator 12c.

The X-ray tube 12a is a vacuum tube that irradiates the subject P with X-ray beams using high voltage supplied from a high-voltage generator (not illustrated). The X-ray tube 12a irradiates the subject P with X-ray beams with rotation of the rotary frame 15. The X-ray tube 12a generates X-ray beams extending at the fan angle and the cone angle. For example, the X-ray tube 12a is capable of making continuous X-ray radiation for the entire circumference of the subject P for full reconstruction and is capable of making continuous X-ray radiation for a radiation range (180 degrees+the fan angle) enabling half reconstruction for half reconstruction under control of the X-ray radiation control circuitry 11. The X-ray tube 12a is further capable of intermittently radiating X-rays (pulse X-rays) at a preset position (a bulb position) under control of the X-ray radiation control circuitry 11. The X-ray radiation control circuitry 11 is capable of modulating intensity of X-ray radiation from the X-ray tube 12*a*. For example, the X-ray radiation control circuitry 11 increases intensity of X-ray radiation from the X-ray tube 12*a* at a certain bulb position and decreases intensity of X-ray radiation from the X-ray tube 12*a* in a range other than the certain bulb position.

The wedge 12*b* is an X-ray filter for adjusting the amount of X-ray radiation from the X-ray tube 12*a*. More specifically, the wedge 12*b* is a filter that passes X-rays radiated from the X-ray tube 12*a* and attenuates the X-rays such that X-ray radiation onto the subject P from the X-ray tube 12*a* has a predetermined distribution. Examples of the wedge 12*b* include a filter made of aluminum worked to have a certain target angle and a certain thickness. The wedge is also referred to as a wedge filter and a bow-tie filter.

The collimator 12*c* is a slit that limits the range of X-ray radiation the amount of which has been adjusted by the wedge 12*b*, under control of the X-ray radiation control circuitry 11.

The gantry driving circuitry 16 rotates the X-ray generator 12 and the detector 13 on a circular orbit with the subject P centered by rotationally driving the rotary frame 15.

The detector 13 is a two-dimensional array detector (an area detector) for detecting X-rays passing through the subject P. In the detector 13, a plurality of rows of detecting elements, which are X-ray detecting elements for a plurality of channels, are aligned along the direction of the body axis (the Z axis direction in FIG. 2) of the subject P. More specifically, the detector 13 according to the second embodiment has X-ray detecting elements aligned in a plurality of rows such as 320 rows along the body axis of the subject P. With this construction, X-rays passing through the subject P can be detected in a wider range such as a range including the lungs and the heart of the subject P.

The data acquisition system (DAS) 14 collects projection data from detection data of X-rays detected by the detector 13. For example, the data acquisition system 14 generates projection data by performing amplification processing, analog-to-digital conversion processing, sensitivity correction processing between channels, and the like on X-ray intensity distribution data detected by the detector 13 and transmits the generated projection data to the later-described console 30. For example, the data acquisition system 14 collects a group of projection data corresponding to the entire circumference (360 degrees) when the X-ray tube 12*a* continuously radiates X-rays during rotation of the rotary frame 15. The data acquisition system 14 further associates each of the collected projection data pieces with the bulb position and transmits the data to the later-described console 30. The bulb position is information indicating a projection direction of projection data. The sensitivity correction processing between channels may be performed by later-described preprocessing circuitry 34.

The table device 20 is a device on which the subject P is laid and includes a table driving device 21 and a tabletop 22 as illustrated in FIG. 10. The table driving device 21 moves the tabletop 22 in the Z axis direction and moves the subject P into the rotary frame 15. The tabletop 22 is a board on which the subject P is laid.

The gantry 10 performs, for example, helical scanning that helically scans the subject P by rotating the rotary frame 15 while moving the tabletop 22. The gantry 10 further performs conventional scanning that scans the subject P on a circular orbit by rotating the rotary frame 15 with the position of the subject P fixed after move of the tabletop 22. The gantry 10 further carries out the step-and-shoot method that performs the conventional scanning in a plurality of scanning areas by changing the positions of the tabletop 22 at regular intervals.

The console 30 is a device that receives operation performed on the X-ray CT apparatus 100 by an operator and reconstructs CT image data using projection data collected by the gantry 10. As illustrated in FIG. 10, the console 30 includes an input interface 31, a display 32, the scan control circuitry 33, the preprocessing circuitry 34, a memory 35, image reconstruction circuitry 36, and processing circuitry 37.

The input interface 31 has a mouse, a keyboard, a trackball, a switch, a button, a joystick, and the like used by the operator of the X-ray CT apparatus 100 for input of various instructions and settings. The input interface 31 forwards instructions and setting information received from the operator to the processing circuitry 37. For example, the input interface 31 receives conditions relating to photography of CT image data, reconstruction conditions under which the CT image data is reconstructed, conditions relating to image processing performed on the CT image data, and others, from the operator. The input interface 31 receives a designation operation for designating a first region of interest and others.

The display 32 is a monitor referred to by the operator. The display 32 displays, to the operator, a CT image generated from the CT image data, a graphical user interface (GUI) for receiving various instructions and settings from the operator through the input interface 31, and others under control of the processing circuitry 37. The display 32 further displays results of the blood flow dynamic analysis and the like.

The scan control circuitry 33 controls processing of collecting projection data performed by the gantry 10 by controlling operation of the X-ray radiation control circuitry 11, the gantry driving circuitry 16, the data acquisition system 14, and the table driving device 21 under control of the processing circuitry 37. Specifically, the scan control circuitry 33 controls photography synchronized with an electrocardiogram received from an electrocardiograph.

The preprocessing circuitry 34 generates corrected projection data by performing logarithmic transformation processing and correction processing such as offset correction, sensitivity correction, and beam-hardening correction on the projection data generated by the data acquisition system 14. More specifically, the preprocessing circuitry 34 generates corrected projection data from each of a projection data piece of a positioning image generated by the data acquisition system 14 and a projection data piece collected through the main photography and stores the data in the memory 35.

The memory 35 stores projection data generated by the preprocessing circuitry 34. More specifically, the memory 35 stores projection data of a positioning image and projection data for diagnosis collected through the main photography, both the projection data being generated by the preprocessing circuitry 34. The memory 35 further stores, for example, CT image data reconstructed by the later-described image reconstruction circuitry 36. The memory 35 further stores results of processing performed by the later-described processing circuitry 37 as appropriate.

The image reconstruction circuitry 36 reconstructs CT image data using projection data stored in the memory 35. More specifically, the image reconstruction circuitry 36 reconstructs CT image data from each of a projection data piece of a positioning image and a projection data piece collected through the main photography. Various methods for reconstruction are applicable including back-projection processing. Examples of back-projection processing include filtered back projection (FBP). The image reconstruction circuitry 36 may reconstruct CT image data using the iterative reconstruction approach.

The image reconstruction circuitry 36 further generates image data by carrying out various kinds of image processing on CT image data. The image reconstruction circuitry 36 stores reconstructed CT image data and image data generated by various kinds of image processing in the memory 35.

The processing circuitry 37 integrally controls the X-ray CT apparatus 100 by controlling operation of the gantry 10, the table device 20, and the console 30. More specifically, the processing circuitry 37 controls CT scanning performed by the gantry 10 by controlling the scan control circuitry 33. The processing circuitry 37 further controls image reconstruction processing and image generation processing performed by the console 30 by controlling the image reconstruction circuitry 36. The processing circuitry 37 further controls the display 32 to display various kinds of image data stored in the memory 35. The processing circuitry 37 has a contrast material injected into the subject P under predetermined conditions by controlling the injector.

The processing circuitry 37 executes a control function 37a, a first setting function 37b, a second setting function 37c, a determining function 37d, and an analyzing function 37e as illustrated in FIG. 10. The control function 37a integrally controls the X-ray CT apparatus 100. The first setting function 37b executes the same processing as that of the above-described first setting function 352. The second setting function 37c executes the same processing as that of the above-described second setting function 353. The determining function 37d executes the same processing as that of the above-described determining function 354. The analyzing function 37e executes the same processing as that of the above-described analyzing function 355.

The CT image data has been described as a target object in the above-described embodiment. The embodiment is, however, not limited thereto, and for example, image data collected by another medical image diagnostic apparatus such as a magnetic resonance imaging (MRI) apparatus may be used as a target object.

In the above-described embodiment, a single processing circuit (the processing circuitry 350 and the processing circuitry 37) implements the processing functions; however, the embodiment is not limited thereto. For example, the processing circuitry 350 and the processing circuitry 37 may be configured by combining a plurality of independent processors, and each processor may execute a computer program and accordingly implement a corresponding processing function. The processing functions of each of the processing circuitry 350 and the processing circuitry 37 may be separately or integrally implemented by a single or a plurality of processing circuits as appropriate.

The term "processor" used in the above-described embodiments indicates a circuit including, for example, a central processing unit (CPU), a graphics processing unit (GPU), an application specific integrated circuit (ASIC), a programmable logic device (for example, a simple programmable logic device (SPLD)), a complex programmable logic device (CPLD), and a field programmable gate array (FPGA). A computer program may be directly embedded in a circuit in a processor instead of being stored in a memory. In this case, the processor implements functions by reading the computer program embedded in the circuit and executing the computer program. Each of the processors in the embodiments is not necessarily configured as a single circuit. The processors may be configured as a single processor by combining a plurality of independent circuits to implement the functions.

The computer program executed by the processor is preliminarily embedded in a read only memory (ROM), a storage unit, or the like and provided. The computer program may be stored in a computer-readable storage medium such as a compact disc (CD)-ROM, a flexible disk (FD), a CD-recordable (CD-R), and a digital versatile disc (DVD) in a file installable or executable by these devices and provided. The computer program may be stored in a computer connected to a network such as the Internet and provided or distributed by being downloaded via the network. For example, the computer program is configured in modules including the later-described function units. Actually, as hardware, each module is loaded onto a main storage device and generated on the main storage device with the CPU reading out the computer program from a storage medium such as a ROM and executing the computer program.

According to at least one of the above-described embodiments, the amount of blood flow can be accurately estimated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
processing circuitry configured to
set a first region of interest in a region corresponding to cardiac muscle on a cross-section of a heart included in image data;
set a second region of interest that is larger than the first region of interest in a region including the region;
determine a threshold for removing noise included in the second region of interest based on a frequency distribution of a signal value in the first region of interest; and
carry out blood flow dynamic analysis on the second region of interest using signal values included in a range based on the threshold.

2. The medical image processing apparatus according to claim 1, wherein the processing circuitry is configured to set the first region of interest by setting a boundary of the cardiac muscle on the cross-section of the heart in a manner excluding a signal other than signal derived from a contrast material flowing into the cardiac muscle.

3. The medical image processing apparatus according to claim 2, wherein the processing circuitry is configured to set the first region of interest by extracting the cardiac muscle on the cross-section of the heart, performing dilation processing on an inner contour corresponding to an inner wall of the extracted cardiac muscle, and performing reduction processing on an outer contour corresponding to an outer wall of the cardiac muscle.

4. The medical image processing apparatus according to claim 3, wherein the processing circuitry is configured to receive an input operation from an operator and perform the dilation processing and the reduction processing in response to the received input operation.

5. The medical image processing apparatus according to claim 2, wherein the processing circuitry is configured to extract the cardiac muscle on the cross-section of the heart, deform a region surrounded by a contour of the extracted cardiac muscle such that a frequency distribution of a signal value in the region surrounded by the contour is approximate to a normal distribution, and set the deformed region as the first region of interest.

6. The medical image processing apparatus according to claim 2, wherein the processing circuitry is configured to set an inner boundary corresponding to an inner wall of the cardiac muscle in a manner excluding a signal derived from a lumen surrounded by the cardiac muscle from a region surrounded by the boundary of the cardiac muscle.

7. The medical image processing apparatus according to claim 2, wherein the processing circuitry is configured to set an outer boundary corresponding to an outer wall of the cardiac muscle in a manner excluding a signal derived from a lumen adjacent to a lumen surrounded by the cardiac muscle from a region surrounded by the boundary of the cardiac muscle.

8. The medical image processing apparatus according to claim 1, wherein the processing circuitry is configured to divide the region into a plurality of partial regions, set the first region of interest in each of the partial regions, and set the second region of interest in each of the partial regions.

9. The medical image processing apparatus according to claim 1, wherein the processing circuitry is configured to determine a threshold for a frequency distribution of a signal value in the first region of interest using a mean value, a standard deviation, or variance and carries out blood flow dynamic analysis on the second region of interest using a signal value lower than the threshold.

10. The medical image processing apparatus according to claim 1, wherein the processing circuitry is configured to cause a display to display a display image including the first region of interest and the second region of interest displayed on the cross-section of the heart.

11. An X-ray Computed Tomography (CT) apparatus comprising:
processing circuitry configured to
collect image data including a heart;
set a first region of interest in a region corresponding to cardiac muscle on a cross-section of the heart included in the image data;
set a second region of interest that is larger than the first region of interest in a region including the region;
determine a threshold for removing noise included in the second region of interest based on a frequency distribution of a signal value in the first region of interest; and
carry out blood flow dynamic analysis on the second region of interest using signal values included in a range based on the threshold.

12. The X-ray CT apparatus according to claim 11, wherein the processing circuitry is configured to set the first region of interest by setting a boundary of the cardiac muscle on the cross-section of the heart in a manner excluding a signal other than signal derived from a contrast material flowing into the cardiac muscle.

13. The X-ray CT apparatus according to claim 12, wherein the processing circuitry is configured to set the first region of interest by extracting the cardiac muscle on the cross-section of the heart, performing dilation processing on an inner contour corresponding to an inner wall of the extracted cardiac muscle, and performing reduction processing on an outer contour corresponding to an outer wall of the cardiac muscle.

14. The X-ray CT apparatus according to claim 13, wherein the processing circuitry is configured to receive an input operation from an operator and perform the dilation processing and the reduction processing in response to the received input operation.

15. The X-ray CT apparatus according to claim 12, wherein the processing circuitry is configured to extract the cardiac muscle on the cross-section of the heart, deform a region surrounded by a contour of the extracted cardiac muscle such that a frequency distribution of a signal value in the region surrounded by the contour is approximate to a normal distribution, and set the deformed region as the first region of interest.

16. The X-ray CT apparatus according to claim 12, wherein the processing circuitry is configured to set an inner boundary corresponding to an inner wall of the cardiac muscle in a manner excluding a signal derived from a lumen surrounded by the cardiac muscle from a region surrounded by the boundary of the cardiac muscle.

17. The X-ray CT apparatus according to claim 12, wherein the processing circuitry is configured to set an outer boundary corresponding to an outer wall of the cardiac muscle in a manner excluding a signal derived from a lumen adjacent to a lumen surrounded by the cardiac muscle from a region surrounded by the boundary of the cardiac muscle.

18. The X-ray CT apparatus according to claim 11, wherein the processing circuitry is configured to divide the region into a plurality of partial regions, set the first region of interest in each of the partial regions, and set the second region of interest in each of the partial regions.

19. The X-ray CT apparatus according to claim 11, wherein the processing circuitry is configured to determine a threshold for a frequency distribution of a signal value in the first region of interest using a mean value, a standard deviation, or variance and carries out blood flow dynamic analysis on the second region of interest using a signal value lower than the threshold.

20. The X-ray CT apparatus according to claim 11, wherein the processing circuitry is configured to cause a display to display a display image including the first region of interest and the second region of interest displayed on the cross-section of the heart.

\* \* \* \* \*